United States Patent [19]

Otten et al.

[11] Patent Number: 5,704,925

[45] Date of Patent: Jan. 6, 1998

[54] MEDICAL INSTRUMENT FOR INJECTING LIQUIDS INTO A HOLLOW ORGAN AND/OR DRAWING OFF LIQUIDS FROM A HOLLOW ORGAN, IN PARTICULAR A BILE DUCT

[75] Inventors: Gert Otten, Schiffdorf; Carsten Lindeke, Berlin, both of Germany

[73] Assignee: Aerztliche Mechanik Udo Lindeke & Sohn, Berlin, Germany

[21] Appl. No.: 385,666

[22] Filed: Feb. 8, 1995

[30] Foreign Application Priority Data

Feb. 9, 1994 [DE] Germany ............... P 44 04 781.9

[51] Int. Cl.$^6$ ............................................. A61M 5/32
[52] U.S. Cl. ............... 604/272; 604/35; 604/115; 606/205; 606/207; 606/208; 606/211
[58] Field of Search ............... 606/167, 205, 606/206, 207, 208, 209, 210, 211, 216, 170, 108; 604/187, 181, 115, 182, 272, 27, 35, 48, 43, 264

[56] References Cited

U.S. PATENT DOCUMENTS

| | | | |
|---|---|---|---|
| 3,019,790 | 2/1962 | Militana | 606/205 |
| 4,011,870 | 3/1977 | Goldstein | 604/272 |
| 4,484,911 | 11/1984 | Berlin et al. . | |
| 4,792,330 | 12/1988 | Lazarus et al. . | |
| 4,817,604 | 4/1989 | Smith, III . | |
| 5,037,430 | 8/1991 | Hasson | 606/208 |
| 5,071,412 | 12/1991 | Noda . | |
| 5,131,379 | 7/1992 | Sewell, Jr. . | |
| 5,176,702 | 1/1993 | Bales et al. | 606/208 |
| 5,209,747 | 5/1993 | Knoepfler | 606/208 |
| 5,224,931 | 7/1993 | Kumar | 606/205 |
| 5,254,095 | 10/1993 | Harvey | 606/210 |
| 5,342,389 | 8/1994 | Haber et al. | 606/205 |
| 5,350,384 | 9/1994 | Clement et al. . | |
| 5,376,094 | 12/1994 | Kline | 606/205 |
| 5,425,705 | 6/1995 | Evard et al. | 604/28 |

FOREIGN PATENT DOCUMENTS

| | | | |
|---|---|---|---|
| 0432560 | 6/1991 | European Pat. Off. | 606/205 |
| 0 519 590 | 12/1992 | European Pat. Off. . | |
| 2 644 056 | 9/1990 | France . | |
| 1382476 | 3/1988 | U.S.S.R. | 606/167 |

Primary Examiner—Michael Powell Buiz
Assistant Examiner—Ronald K. Stright, Jr.
Attorney, Agent, or Firm—McAulay Fisher Nissen Goldberg & Kiel, LLP

[57] ABSTRACT

Medical instrument for injecting liquids into a hollow organ and/or drawing off liquids from a hollow organ, in particular a bile duct. Clamping apparatus are associated with the hollow needle of the instrument, this instrument being constructed as a tubular shaft, and the tissue of the hollow organ can be securely enclosed by these clamping apparatus between an entrance opening in the hollow organ and an outlet opening of the hollow needle in such a way that no liquid can escape between the tissue and the hollow needle.

13 Claims, 2 Drawing Sheets

MEDICAL INSTRUMENT FOR INJECTING LIQUIDS INTO A HOLLOW ORGAN AND/OR DRAWING OFF LIQUIDS FROM A HOLLOW ORGAN, IN PARTICULAR A BILE DUCT

BACKGROUND OF THE INVENTION a) Field of the Invention

The invention is directed to a medical instrument employing a hollow needle for injecting liquid into and/or removing liquid from a hollow organ.

b) Description of the Related Art

In instruments of this type, which are already known, a sharp hollow needle is stuck into the cavity or lumen. For this purpose, the hollow organ is fixed in place in the region of puncture in a holder associated with the shaft of the instrument and the hollow needle guided by the shaft is inserted into the organ approximately vertically. In many cases, it is very difficult to access the lumen with precision, particularly when the hollow organ is a bile duct, for example. Often, more than one wall of the hollow organ will be penetrated so that the hollow needle does not go into the lumen, but exits again at the other side.

Further, it is known to insert a substantially flexible tube into an opening which has been prepared in the lumen beforehand and to inject or draw off liquid via the tube. In the first place, insertion of the tube is often problematic. On the other hand, an escape of liquid between the tube and the opening of the hollow organ cannot be ruled out.

OBJECT AND SUMMARY OF THE INVENTION

The primary object of the present invention is to provide a medical instrument of the type mentioned above which permits liquid to be injected or drawn off accurately and without losses and which is easy to handle and can be produced economically.

This object is met, according to the invention, in that a clamping device is associated with a hollow needle, by means of which the tissue of the hollow organ can be enclosed and pressed against the hollow needle at least between the previously prepared incision or entrance opening of the hollow organ and an outlet opening of the hollow needle. Accordingly, the annular gap between the hollow needle and the tissue is reliably sealed such that no liquid can pass through this gap. In this way, liquids can easily be injected or drawn off, in particular injected into or drawn out of small hollow organs such as bile ducts, without losses.

A free end of the hollow needle is preferably bent. The bent insertion part facilitates arrangement of the free end within the bile duct and enables a dependable sealing in the region of the insertion part and consequently within a longer portion of the bile duct. The bent arrangement of the insertion part assists lateral insertion and placement of the hollow needle and clamping device.

In a further development of the invention, the clamping device is a pair of clamping forceps whose jaws are movable relative to one another in such a way that the tissue and hollow needle can be securely enclosed by a forceps mouth in the clamping position of the forceps and released in the initial position of the forceps. The sealed arrangement of the hollow needle in the bile duct can be ensured by the movement of the clamping jaws by itself and consequently in a very simple manner.

In an advantageous development, one jaw ends in two prongs arranged in the shape of a fork and the other jaw ends in one prong. These prongs form the forceps mouth, the prong of one jaw being arranged between the two prongs of the other jaw in the clamping position of the forceps so that the prongs mesh with one another to a certain extent. Due to the meshing of the prongs, which are quite narrow, the tissue is held in place near the hollow needle so as to be centered regardless of the shape or thickness of the tissue and irrespective of an asymmetrical arrangement of this tissue around the hollow needle.

It is advisable that at least the prongs extend in a roughly curved manner in the direction of the hollow needle so that the tissue is pressed against the hollow needle in the radial direction of the insertion part in an approximately uniform manner around the circumference of the hollow needle. It is advantageous with respect to sealing that only a short longitudinal portion of the insertion part is required for reliably holding and sealing the tissue.

In a further development of the invention, a base body of the forceps extends adjacent to the hollow needle. This base body emerges from a head of a tubular shaft substantially parallel to the hollow needle and, like the latter, eccentrically relative to the shaft. The jaws of the forceps are articulated at the base body so as to be swivelable in opposite directions in such a way that the forceps mouth always encloses the hollow needle and tissue in the region of the insertion part of the hollow needle. Accordingly, sealing is effected in a compulsory manner between the entrance opening prepared beforehand in the hollow organ and the outlet opening of the hollow needle. Liquid can be injected into the hollow organ or drawn out of it without losses due to lack of tightness between the tissue and hollow needle.

Additional features of the invention and their advantages are contained in the rest of the claims and in the description. The invention is explained more fully in the following with reference to an embodiment example.

DESCRIPTION OF THE PREFERRED EMBODIMENTS

Figure 1:
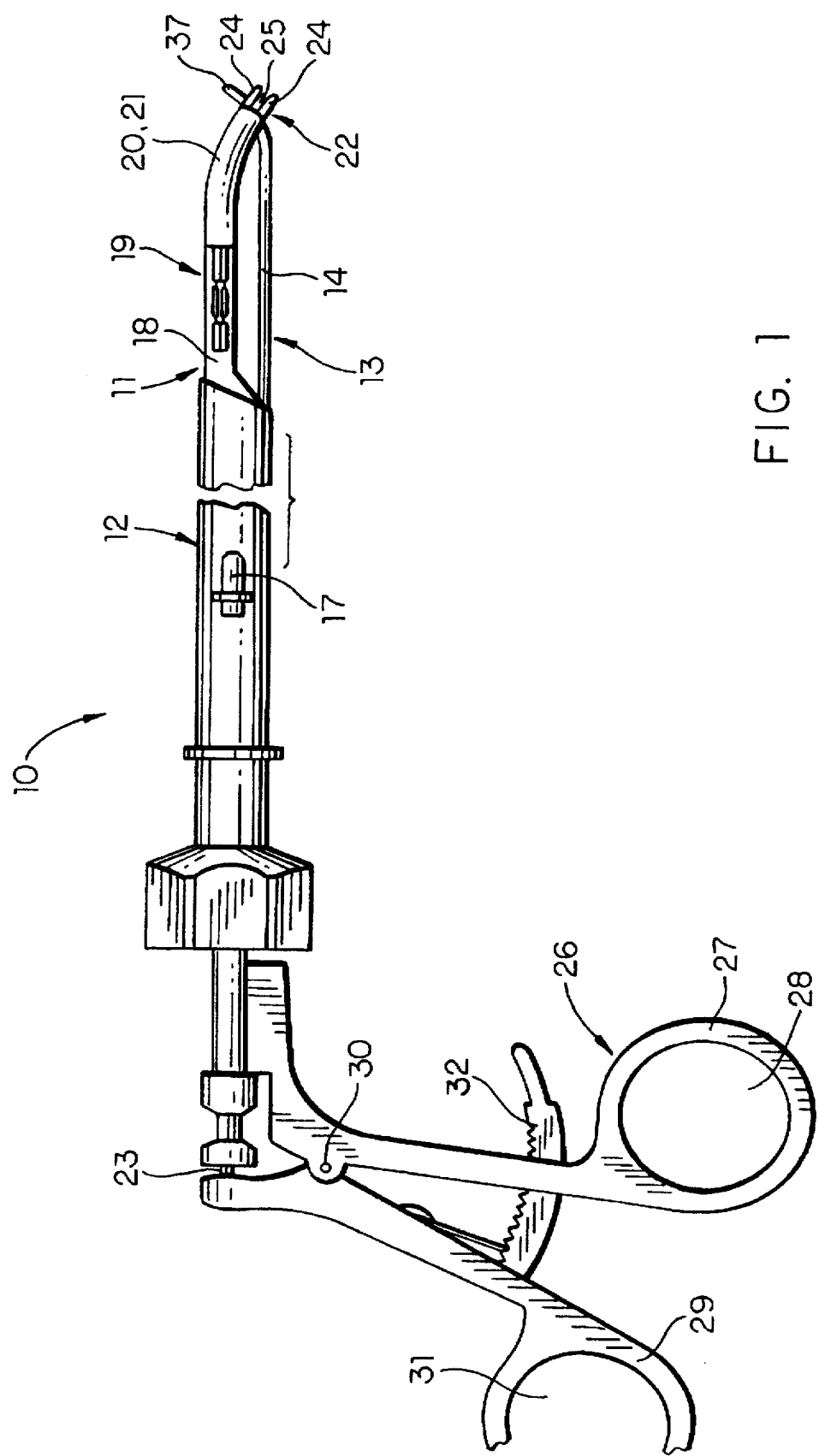
FIG. 1 illustrates a schematic side view of the medical instrument.

A medical instrument 10 (FIG. 1) for injecting liquids into a hollow organ, e.g., a bile duct, and drawing liquids out of a hollow organ is constructed as a tubular shaft instrument. A hollow needle 13 emerges from a head 11 of a tubular shaft 12 at one end of the latter. This hollow needle 13 extends from the tubular shaft 12 and from its lower periphery substantially parallel and eccentrically thereto. A free end 14 of the hollow needle 13 is bent near an outlet opening 15 in the direction of the line of symmetry of the tubular shaft 12 so as to form an insertion part 16 of the hollow needle 13. The hollow needle 13 can accordingly be inserted laterally into the bile duct via an entrance opening made in the bile duct beforehand and can be positioned in a reliable manner approximately coaxially within the bile duct by means of the insertion part 16.

A connection 17 exits from a central region of the tubular shaft 12 and is connected with the hollow needle 13 so that liquid, e.g., contrast media, can be injected via the connection 17 into the bile duct and, as the case may be, drawn out again after the bile duct has been x-rayed. It is possible to draw out bile in the same manner.

A base body 18 of a clamping device constructed as forceps 19 also emerges from the head 11 of the tubular shaft 12 at its periphery located opposite the hollow needle 13 and approximately parallel to the hollow needle 13. The forceps 19 serve to press the tissue of the bile duct disposed around the insertion part 16 of the inserted hollow needle 13 firmly against this insertion part 16 so as to achieve a seal which prevents liquid from escaping between this tissue and the hollow needle 13. Sealing is effected in that the tissue is pressed against the hollow needle 13 between the outlet opening 37 of the hollow needle 13 and the entrance opening. Among other things, this enables unambiguous and verifiable detection of the bile duct leading to the gallbladder, which is of crucial importance before continuing with a surgical procedure.

The forceps 19 have two jaws 20, 21 which are articulated at the base body 18 so as to be swivelable in opposite directions. The swiveling movement is initiated by means of a rod linkage 23 which extends along the base body 18 and exits from the base body 19 and tubular shaft 12 on the side located opposite the jaws 20, 21. The jaws 20, 21 are arranged in such a way that the hollow needle 13 and the tissue located in that area are firmly enclosed in the region of the insertion part 16 by a mouth 22 of the forceps 19 in the clamping position or released in the initial position.

The forceps mouth 22 is formed by two prongs in a fork-like arrangement and by a prong 25. One jaw 20 ends in the two prongs 24 while the other jaw 21 ends in prong 25. In the clamping position of the forceps 19, prong 25 is arranged between prongs 24 so that these prongs mesh with one another to a certain extent. In this way, the insertion part 16 of the hollow needle 13 and the enclosed tissue are centered and firmly grasped. The centering is effected between the prongs 24, 25 and not far from the region of jaw 20 from which prongs 24 extend in a fork-like manner.

Figure 2:
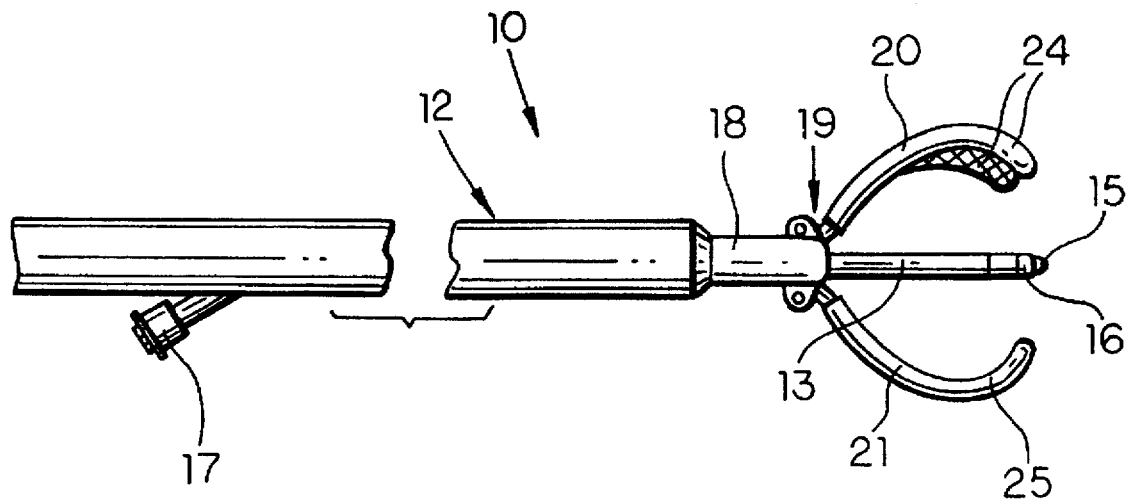
FIG. 2 illustrates a schematic top view of the instrument according to FIG. 1 with forceps arranged in the initial position.
Figure 3:
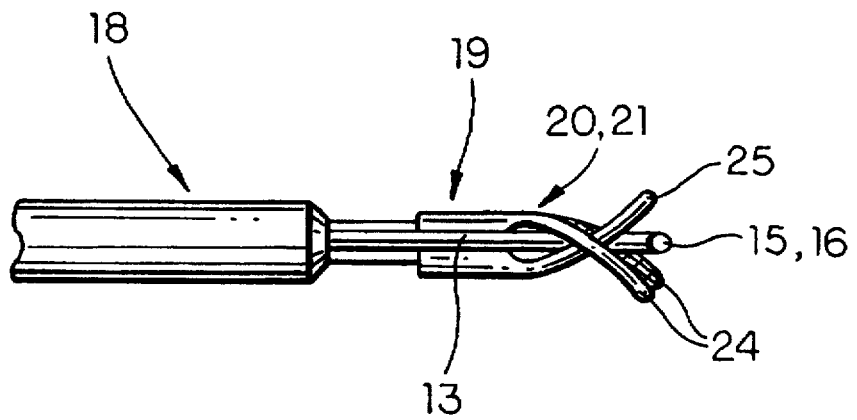
FIG. 3 illustrates a partial top view according to FIG. 2 with forceps arranged in the clamping position.

The jaws 20, 21 and their prongs 24, 25 are constructed so as to be curved in their plane of movement as will be seen from FIG. 2 in particular. One prong 24 of jaw 20 is shifted forward somewhat in the drawing so as to show its fork-like construction more clearly. Accordingly, due to the design of the jaws 20, 21 and the articulation at the base body 18, the prongs 24, 25 are movable in a swiveling manner, e.g., similar to pincers.

The forceps 19 and their jaws 20, 21 and prongs 24, 25 have small dimensions in the radial direction of the tubular shaft 12, at least when the forceps 19 are in the clamping position, this radial dimension being smaller than the inner diameter of a trocar used in laparoscopic procedures so that the present device can also be used in a procedure of this kind.

Further, the prongs 24, 25 are additionally deflected in a curved manner in the direction of the insertion part 16 of the hollow needle 13. This deflection roughly corresponds to the bending of the hollow needle 13, but is effected in the direction of the hollow needle 13 and accordingly to a certain extent in the opposite direction of the bend. This construction of the jaws 20, 21 and prongs 24, 25 ensures that the hollow needle 13 and the tissue of the hollow organ will be pressed against the circumference of the insertion part 16 in a virtually uniform manner approximately in the radial direction of the insertion part 16. Accordingly, a reliable sealing is always provided regardless of the shape and thickness of tissue.

The surface of the prongs 24, 25, at least that portion making contact with the tissue, can also be profiled, e.g., knurled. In this way, the holding of the tissue within the forceps mouth 22 can be further improved.

A scissor-like handle 26 is arranged at that end of the base body 18 of the forceps 19 located opposite the jaws 20, 21 where this base body 18 emerges from the tubular shaft 12. This handle 26 is used to hold the medical instrument 10 and also to actuate the jaws 20, 21 of the forceps 19. On the side remote of a finger grip 28, one half 27 of the handle is connected in a stationary manner with the end of the base body 18 on this side. Another half 29 is movable relative to the latter so as to swivel about an arbor 30. The rod linkage 23 is articulated at handle half 29 on the side located opposite the finger grip 31. During a swiveling movement of the handle halves 27, 29 about the arbor 30, the rod linkage 23 is displaced in the axial direction along the base body 18 and tubular shaft 12, whereupon the swiveling movement of the jaws 20, 21 in opposite directions from the initial position to the clamping position, and vice versa, can be effected. In order to realize this relative movement of the jaws 20, 21, these jaws and a corresponding region of the rod linkage 23 are connected via a scissor lever mechanism. However, they can also be constructed partially as complementary members of a rack-and-pinion mechanism or the like.

Finally, a retaining device 32, known per se, is associated with the handle halves 27, 29. The handle halves 27, 29 and accordingly also the jaws 20, 21 can be fixed in a position corresponding to the clamping position or initial position of the forceps 19 by means of this retaining device 32.

While the foregoing description and drawings represent the preferred embodiments of the present invention, it will be obvious to those skilled in the art that various changes and modifications may be made therein without departing from the true spirit and scope of the present invention.

What is claimed is:

1. A medical instrument for injecting liquid into a hollow organ and/or drawing off liquid from a hollow organ, such as a bile duct comprising:

a shaft;

a hollow needle which can be inserted at a free end thereof into the hollow organ via an entrance opening of the organ, said needle being mounted within said shaft; and clamping means associated with the hollow needle and mounted within said shaft for enclosing the tissue of the hollow organ, said clamping means for clamping at least between an entrance opening of the hollow organ and an outlet opening of the hollow needle at said free end thereof so that no liquid can escape between the tissue and the hollow needle;

wherein said free end of the hollow needle includes a curved insertion region and the tissue can be sealed against the hollow needle in the curved insertion region of said needle by said clamping means.

2. The medical instrument according to claim 1, wherein the clamping means include forceps having jaws movable relative to one another in such a way that the hollow needle and tissue are securely enclosed by a forceps mouth in a clamping position or are released in an initial position, said instrument including means to operate said forceps.

3. The medical instrument according to claim 2, wherein the forceps mouth is formed by at least one prong of each jaw and the prongs are arrangable so as to mesh with one another.

4. The medical instrument according to claim 3, wherein one jaw ends in two prongs arranged in the shape of a fork and the other jaw ends in one prong which engages in the fork-shaped prongs in a clamping position.

5. The medical instrument according to claim 4, wherein at least the prongs extend in a roughly curved manner in the direction of the hollow needle so that the hollow needle and tissue can be enclosed in the radial direction of said insertion region of said needle and in an approximately uniform manner around the circumference of the hollow needle.

6. The medical instrument according to claim 5, wherein the prongs are deflected in the direction of said insertion part of the hollow needle and the deflection roughly corresponds to the curvature of the hollow needle in the opposite direction.

7. The medical instrument according to claim 4, wherein at least one prong surface is profiled so as to securely hold the tissue.

8. The medical instrument according to claim 2, wherein said shaft is tubular, wherein said forceps include a base body; said base body of the forceps being mounted within the tubular shaft, the forceps extending adjacent to the hollow needle and emerging from the head of a tubular shaft, the jaws of the forceps being articulated at the base body so as to be swivelable in opposite directions.

9. The medical instrument according to claim 8, including a handle for holding the instrument and operating said forceps, said handle being of scissor-like form, one half of said scissor-like handle being connected in a stationary manner with the base body and wherein a rod linkage for actuating the jaws of the forceps is articulated at another half of the handle which swivels relative to the other half.

10. The medical instrument according to claim 9, wherein a retaining device is mounted on at least one of the handles so as to fix the handle halves and jaws in a defined manner relative to one another.

11. The medical instrument according to claim 8, including a handle mounted on said clamping means for holding the instrument and actuating the forceps, said handle being arranged at the end of a tubular shaft located opposite the jaws.

12. The medical instrument according to claim 1, wherein said shaft is tubular, wherein a free end of said hollow needle emerges from an end of the tubular shaft and said needle extends parallel and eccentrically relative to the tubular shaft.

13. The medical instrument according to claim 12, wherein a connection exits from a central region of said tubular shaft and is connected with the hollow needle and liquid can be directed into or out of the hollow needle by way of said connection.

* * * * *